United States Patent [19]
Kriegler et al.

[11] Patent Number: 5,702,705
[45] Date of Patent: Dec. 30, 1997

[54] ANTIBODY METHODS FOR THE TREATMENT OF A HORMONE-MEDIATED DISEASE

[75] Inventors: Michael Kriegler, San Francisco; Carl Perez, Berkeley, both of Calif.

[73] Assignee: Chiron Corporation, Emeryville, Calif.

[21] Appl. No.: 463,892

[22] Filed: Jun. 5, 1995

Related U.S. Application Data

[62] Division of Ser. No. 424,243, Apr. 18, 1995.

[51] Int. Cl.$^6$ .................. A61K 39/395; C07K 16/00; C07K 16/26; C07K 16/24
[52] U.S. Cl. .................. 424/145.1; 424/130.1; 424/141.1; 424/158.1; 424/133.1; 424/134.1; 530/387.1; 530/387.3; 530/388.1; 530/388.23; 530/388.24; 530/388.85; 435/325; 435/328; 435/335; 435/336; 435/344.1
[58] Field of Search .................. 424/130.1, 145.1; 435/240.27, 325, 328, 335, 336, 344.1; 530/387.1, 388.1, 388.23, 388.24, 387.3, 388.85

[56] References Cited

U.S. PATENT DOCUMENTS

| | | |
|---|---|---|
| 4,474,893 | 10/1984 | Reading . |
| 4,870,163 | 9/1989 | Rubin et al. . |
| 5,231,024 | 7/1993 | Moeller et al. .......... 435/240.27 |

FOREIGN PATENT DOCUMENTS

| | | |
|---|---|---|
| 0 288 088 | 10/1988 | European Pat. Off. . |
| 0 351 789 | 1/1990 | European Pat. Off. . |
| WO 91/02078 | 2/1991 | WIPO . |

OTHER PUBLICATIONS

Beutler, B. et al., Science, 229:869–871, 1985.
Fendley, B. M. et al, Hybridoma, 6(4):359–370, 1987.
Kriegler, M. et al, Cell, 53:45–53, Apr. 8, 1988.
Chistou, N.v. et al, Perspectives in Shock Research, 264:115–124, 1988.
Aggarwal et al., "Human Tumor Necrosis Factor," *The Journal of Biological Chemistry*, 260(4):2345–2354 (Feb. 25, 1985).
Bringman et al., "Monoclonal Antibodies to Human Tumor Necrosis Factors Alpha and Beta: Application for Affinity Purification, Immunoassays, and as Structural Probes," *Hybridoma*, 6(5):489–507 (1987).
Decker et al., "Cell–Associated Tumor Necrosis Factor (TNF) As A Killing Mechanism of Activated Cytotoxic Macrophages," *The Journal of Immunology*, 138(3):957–962 (Feb. 1, 1987).

Fendly et al., "Murine Monoclonal Antibodies Defining Neutralizing Epitopes on Tumor Necrosis Factor," *Hybridoma*, 6(4):359–370 (1987).
Jemmerson et al., "Monoclonal antibodies block the trypsin cleavage site on human placental alkaline phosphatase," *FEBS* 173(2):357–359 (Aug. 1984).
Kohler, et al., "Continuous cultures of fused cells secreting antibody of predefined specificity," *Nature*, 256:495–499 (Aug. 7, 1975).
Kriegler et al., "A Novel Form of TNF/Cachectin Is A Cell Surface Cytotoxic Transmembrane Protein: Ramifications for the Complex Physiology of TNF," *Cell*, 53:45–53 (Apr. 8, 1988).
Milstein, C., et al., *Immun. Today*, 5(10):299–304 (1984).
Pennica et al., "Human tumor necrosis factor: precursor strcture, expression and homology to lymphotoxin," *Nature*, 312:724–729 (Dec. 1984).
Scuderi, P., "Suppression of Human Leukocyte Tumor Necrosis Factor Secretion by the Serine Protease Inhibitor p–Toluenesulfonyl–L–Arginine Methyl Eser (TAME)", *The Journal of Immunology*, 143(1):168–173 (Jul. 1, 1989).
Shimamoto et al., "Monoclonal antibodies against human recombinant tumor necrosis factor: prevention of endotoxic shock," *Immunology Letters*, 17:311–318 (1988).
Socher et al., "Antibodies against amino acids 1–15 of tumor necrosis factor block its binding to cell–surface receptor," *Proc. Natl. Acad. Sci. USA*, 84:8829–8833 (Dec. 1987).
Steiner et al., "Use of a synthetic peptide antigen to generate antisera reactive with a proteolytic processing site in native human proinsulin: Demonstration of cleavage within clathrin–coated (pro)secretory vesicle," *Proc. Natl. Acad. Sci. USA*, 84:6184–6188 (Sep. 1987).
Tooze et al., "An Antibody Specific for an Endoproteolytic Cleavage Site Provides Evidence That Pro–opiomelanocortin Is Packaged Into Secretory Granules in AtT20 Cells before Its Cleavage," *The Journal of Cell Biology*, 105:155–162 (1987).
Tracy et al., "Anti–cachectin/TNF monoclonal antibodies prevent septic shock during lethal bacteraemia," *Nature*, 330:662–664 (Dec. 17, 1987).

*Primary Examiner*—Susan A. Loring
*Attorney, Agent, or Firm*—Donald J. Pochopien; Paul B. Savereide; Robert P. Blackburn

[57] ABSTRACT

Cleavage site blocking antibody that binds to prohormones, preferable Tumor Necrosis Factor, thereby preventing the formation of prohormone fragment(s) by proteolysis of the prohormone, and uses of the antibody including prophylactic and therapeutic methods to treat disease, and diagnostic assays for determining the amount of the prohormone and prohormone fragments present in a patients body.

8 Claims, No Drawings

ANTIBODY METHODS FOR THE TREATMENT OF A HORMONE-MEDIATED DISEASE

This application is a division of U.S. Ser. No. 08/424,243, filed Apr. 18, 1995, now pending, which is a file wrapper continuation of U.S. Ser. No. 08/112,600, filed Aug. 26, 1993, now abandoned, which is a continuation of U.S. Ser. No. 07/395,254, filed Aug. 16, 1989, now abandoned.

TECHNICAL FIELD

This invention is in the area of immunology/biochemistry, and presents the development of antibody, preferably monoclonal antibody, that prevents the formation of mature protein hormones from prohormone precursors by binding to the prohormones thereby blocking specific sites that are cleaved by proteolytic enzymes. The antibody has diagnostic, and prophylactic and therapeutic applications for treating diseases, particulary sepsis and AIDS, associated with elevated levels of mature hormones.

BACKGROUND OF THE INVENTION

Tumor Necrosis Factor (TNF) is a cytokine which is known to have cytolytic and cytostatic anti-tumor activity. Carswell, et al. (1975) Proc. Nat'l Acad. Sci. U.S.A. 72: 3666–3670; Williamson, et al. (1983) Proc. Nat'l Acad. Sci. 80: 5397–5401. In addition it has recently been shown to be a mediator in the immunoinflammatory cascade and play a key role in sepsis. Beutler, et al. (1985) Science 229: 869, reported that in a murine model the lethal effect of endotoxin can be reduced by polyclonal rabbit anti-murine TNF antibody. In the United States alone nosocomial bacteremia develops in about 194,000 patients, and of these about 75,000 die. Maki, D. G., 1981, *Nosocomial Infect.*, (Dikson, R. E., Ed.), page 183, Yrke Medical Books, U.S.A. Most of these deaths are attributable to six major gram-negative bacilli, and these are *Pseudomonas aeruginosa, Escherichia coli*, Proteus, Klebsiella, Enterobacter and Serratia. The current treatment for bacteremia is the administration of antibiotics which, unfortunately, have limited effectiveness.

Although the precise pathology of bacteremia is not completely elucidated, it is known that bacterial endotoxins, lipopolysaccharides (LPS), are the primary causative agents. LPS consist of at least three significant antigenic regions, the lipid A, core polysaccharide, and O-specific polysaccharide. The latter is also referred to as O-specific chain or simply O-antigen. The O-specific chain region is a long-chain polysaccharide built up from repeating polysaccharide units. The number of polysaccharide units differs among different bacterial species and may vary from one to as many as six or seven monosaccharide units. While the O-specific chain varies among different gram-negative bacteria, the lipid A and core polysaccharides are similar if not identical.

Since LPS plays a key role in sepsis, a variety of approaches has been pursued to neutralize its activity. Presently, there is considerable work which suggest that antibody to LPS will soon be a valuable clinical adjunct to the standard antibiotic therapy.

LPS initiates a cascade of biochemical events that eventually causes the death of the patient. It is widely believed that the second event, after the introduction of LPS, is the production of tumor necrosis factor (TNF) as a result of LPS stimulation of macrophage cells. Thus, considerable effort has been expended to produce neutralizing antibody to TNF, or other molecules that could inhibit its septic effects. It is likely that antibody to TNF will have valuable clinical applications. Tracey, et al., 1987, *Nature*, 330:662.

TNF has been shown to exist in both membrane bound and soluble secreted forms. Decker, et al., 1987, *J. of Immunol.*, 138:957; Kriegler, et al., 1988, *Cell*, 53:45. Human TNF has been cloned and shown to consist of a 17 kd polypeptide, plus an unusually long 76 amino acid putative signal leader sequence. The 17 kd molecule is a key agent involved in initiating the biochemical cascade responsible for sepsis. It has been proposed by Kriegler, et al., 1988, *Cell*, 53:45, that TNF may exist as both a membrane bound 26 kd form, and a soluble form corresponding to the 17 kd species. The 26 kd form is the precursor, or prohormone, of the mature 17 kd molecule. The 17 kd form of TNF plays a central role in causing sepsis. It has been proposed by Kriegler, et al. above, that the two forms of TNF may have different biological effects, although what these might be was not stated.

TNF, in addition to playing a critical role in sepsis, has recently been shown to be involved in initiating the expression of human immunodeficiency virus in human cells that carry latent virus. Folks et al., Proc. Natl. Acad. Sci. U.S.A., vol. 86, p. 2365 (1989). Thus, preventing or inhibiting the formation of the 17 kd, or lower molecular weight forms of TNF from its 26 kd precursor, would be an effective way of curing AIDS patients that harbor latent virus by preventing the virus from being expressed.

Because TNF is involved in causing disease, inhibitors of its action are keenly sought after. In addition to anti-TNF antibody mentioned above, other molecules with TNF inhibitory activity have been identified. One such non-antibody TNF inhibitor is described by Seckinger, et al., 1988, *J. Exp. Med.*, 167:1511. It is present in the urine of febrile patients, but, unfortunately, it has not been purified and characterized to the point where it is clinically useful.

The immunopathogenic properties of TNF makes desirable the accurate monitoring of biologically active 17 kd TNF in a patient's serum. Currently, 17 kd TNF is measured by a laborious in vitro cytotoxicity assay employing mouse fibroblast cells, or using antibody directed to the 17 kd species. Since the 17 kd molecule is derived from 26 kd TNF, more informative and predictive of the course of a patients disease would be the ratio of 26 kd TNF to the 17 kd form. At present, there is no reliable assay for the 26 kd molecule.

SUMMARY OF THE INVENTION

A first object of the invention is a description of antibody, both polyclonal and monoclonal, that prevents or reduces the rate of formation of hormones from their prohormone precursors by binding to a region on the prohormone that either directly or indirectly sterically hinders access of proteases to cleavage sites that yield the hormone.

A second object of the invention is a description of antibody, polyclonal or monoclonal, that directly prevents or reduces the rate of formation of lower molecular weight forms of TNF from its 26 kd prohormone precursor by binding to epitopes on the 26 kd molecule that are proteolyzed to yield lower molecular weight TNF forms, thereby blocking proteolysis at these sites.

A third object of the invention is a description of antibody, polyclonal or monoclonal, that indirectly prevents or reduces the rate of formation of lower molecular weight forms of TNF from its 26 kd prohormone precursor by binding to an epitope(s) remote from the cleavage sites on the 26 kd prohormone, and thereby blocks proteolysis at these site(s) by steric hinderance.

A fourth object of the invention is a description of an immunoassay that measures both 17 kd and 26 kd TNF in a fluid sample, such as blood. In a preferred embodiment, the antibody is neutralizing and thus provides a measure of biologically active TNF in the sample.

These, and other objects of the invention, will be more fully understood after a consideration of the following description of the invention.

DETAILED DESCRIPTION OF THE INVENTION

The present invention is directed broadly to the production of prohormone antibody, preferably high affinity polyclonal or monoclonal antibody, that prevents or reduces the formation of a hormone from its prohormone precursor. The invention is also directed to the utilization of such antibodies in immunoassays as well as for the treatment of parasitic diseases. Several patents/patent applications and scientific references are referred to below. Because the invention draws on the materials and methods shown in these references, it is thus intended that all of the references, in their entirety, be incorporated by reference.

To more clearly define the present invention, particular terms herein will be employed according to the following definitions generally consistent with their usage in the art.

The terms "prohormone", and "mature hormone" have the following meanings. Prohormone is intended to cover proteins, preferably of immunologic origin, that have a peptide segment of the protein removed during its production. The removal of the peptide yields the "mature" form of the hormone. The preferred embodiment of the invention is the 26 kd TNF prohormone, as discussed in detail below, which is cleaved primarily to a 17 kd mature form. However, other cleavage products are also formed from the prohormone, and these are intended to come within the meaning of "mature" hormone. Finally, it is important to note, that prohormones in addition to TNF are intended to come within the scope of these definitions and are considered a part of the invention. Exemplary prohormones are the CSFs and Il-1.

"Monoclonal antibody" refers to a composition of antibodies produced by a clonal population (or clone) derived through mitosis from a single antibody-producing cell. A composition of monoclonal antibodies is "substantially free of other antibodies" when it is substantially free of antibodies that are not produced by cells from the clonal population. The term "substantially free" means approximately 5% (w/w) or fewer contaminating antibodies in the composition.

"Cleavage site blocking antibody" refers to antibody that binds to TNF prohormone, and inhibits or prevents cleavage of the prohormone to lower molecular weight fragments. Binding may be at the cleavage site(s) or remote therefrom.

An "antibody-producing cell line" is a clonal population or clone derived through mitosis of a single antibody-producing cell capable of stable growth in vitro for many generations.

"Tumor Necrosis Factor" or "TNF" as used herein refers to both native and recombinant forms of this known, mammalian cytokine. TNF has been referred to by other names in the literature, including "Cachectin" and "TNF-a". "Recombinant TNF" or "rTNF" refers to proteins, including muteins, produced by expression of recombinant DNA that have the same or substantially the same amino acid sequence as native TNF (or portions thereof), and retain both the in vitro and in vivo biological activity of TNF. The isolation and production of both native and recombinant mammalian TNF, including human TNF, is known in the art. See, e.g., Carswell et al. (1975) Proc. Nat'l Acad Sci. U.S.A. 72: 3666–3670; Williamson et al. (1983) Proc. Nat'l Acad. Sci. U.S.A. 80: 5397–5401; Wang et al. (1985) Science 228: 149–154; Beutler et al. (1985) J. Exp. Med. 161: 984; Beutler et al. (1985) Science 229: 869; Beutler et al. (1985) Nature 316: 552; Pennicia et al. (1984) Nature 312: 724; Aggarwal et al. (1985) J. Biol. Chem. 260: 2345.

As used herein, TNF having a molecular weight of about 26,000, refers to the prohormone form of TNF. It is known that the amino-terminal peptide of the prohormone varies in length depending on the species from which it is derived, while the propeptide segment of the molecule is highly conserved. Indeed, in the mouse approximately 86% of the 79 amino acids that makeup the putative leader sequence of the pro-hormone are identical to the 76 known amino acids that comprise the pro-sequence of human TNF. Thus, it will be appreciated by those skilled in the art that when reference is made below to TNF having a molecular weight of about 26,000, that what is indicated is a molecule that is not derived from a particular species and that may have a slightly altered leader sequence compared to the human sequence as is known in the art.

Sepsis is herein defined to mean a disease resulting from bacterial infection due to the bacterial endotoxin, lipopolysaccharide (LPS). It can be induced by at least the six major gram-negative bacilli and these are *Pseudomonas aeruginosa, Escherichia coli,* Proteus, Klebsiella, Enterobacter and Serratia. TNF is one factor that contributes to the early phase of the disease, and more particularly the 17 kd form of the molecule, or shorter muteins know in the art, are the primary active species.

The term "convertase", or "TNF convertase" is meant to encompass an enzyme normally present in the body that is responsible for proteolytic cleavage of 26 kd TNF to one or more lower molecular weight species. The convertase is substantially membrane associated, although significant activity is located in the cytosol.

The phrase "membrane associated" as applied to TNF convertase indicates a form of the convertase that is substantially insoluble as indicated by the presence of most of the convertase activity in a 30,000×g pellet fraction.

"Recombinant antibody" refers to antibody wherein one portion of each of the amino acid sequences of heavy and light chain is homologous to corresponding sequences in antibody derived from a particular species or belonging to a particular class, while the remaining segment of the chains is homologous to corresponding sequences in another. Most commonly, in a recombinant antibody the variable region of both light and heavy chain mirrors the variable regions of antibody derived from one species of mammals, while the constant regions are homologous to the sequences in antibody derived from another.

Two antibodies are "cross-blocking" or have a "shared epitope" when each antibody effectively blocks the binding of the other antibody in a binding inhibition assay. Thus, if antibodies A and B are cross-blocking, antibody A would not bind to its antigen when the antigen had been preincubated with antibody B, and antibody B would not bind to its antigen when the antigen had been preincubated with antibody A.

The term "binding affinity" or "Ka" of an antibody to its epitope, as used herein, refers to a binding affinity calculated according to standard methods by the formula $Ka=8/3(It-Tt)$, where It is the total molar concentration of inhibitor uptake at 50% tracer, and Tt is the total molar concentration of tracer. See Muller, (1980) J. Immunol. Methods 34: 345–352.

As used herein, the term "incubation" means contacting antibodies and antigens under conditions that allow for the formation of antigen/antibody complexes (e.g., proper pH, temperature, time, medium, etc.). Also as used herein, "separating" refers to any method, usually washing, of separating a composition from a test support or immobilized antibody, such that any unbound antigen or antibody in the composition are removed and any antigen/antibody complexes on the support remain intact. The selection of the appropriate incubation and separation techniques is within the skill of the art.

I. Cleavage Site Blocking Anti-26 kd Antibody

In a preferred embodiment, anti-TNF antibody producing immunologic cells are isolated from a mammal immunized with 26 kd TNF, and immortalized to yield antibody secreting hybridoma cell lines. Cell lines that secrete anti-26 kd TNF that prevent or hinder cleavage of the molecule to lower molecular weight forms of TNF can be identified by assaying culture supernatants for the desired antibody in the presence of a convertase enzyme that cleaves the 26 kd molecule. Thus, the invention can be broken down into 3 sections, and each section discussed separately.

A. 26 kd TNF Immunogen

Antibody that blocks the cleavage site(s) on the 26 kd molecule can be produced using cells, tissues etc., as immunogen that express the 26 kd molecule. Examples would include biological agents known in the art to express 26 kd TNF, such as stimulated monocytes, as described by Kriegler, et al., 1988, in Cell, 53:45, leukocytes, or cell lines of leukocyte origin. The procedures for isolating monocytes are well known in the art, as are methods for culturing cell lines.

A second, and preferred approach is to synthesize peptides, herein after termed TNF peptides, that are recognized by the convertase, and use these as immunogens. The methods for making antibody to peptides are well known in the art and generally require coupling the peptide to a suitable carrier molecule, such as serum albumin. The preferred peptides are Gln-Ala-Val-Arg-Ser-Ser-Ser, Gln-Ala-Val-Arg-Ser-Ser-Ser-Arg-Thr-Pro-Ser-Asp-Lys-Pro-Val-Ala, Pro-Leu-Ala-Gln-Ala-Val-Arg-Ser-Ser-Ser-Arg-Thr-Pro-Ser-Asp-Lys-Pro-Val-Ala-His-Val-Val-Ala, Arg-Thr-Pro-Ser-Asp-Lys-Pro-Val-Ala-His-Val-Val-Ala, and Pro-Leu-Ala-Gln-Ala-Val-Arg-Ser-Ser-Ser-Arg-Thr-Pro. The peptides can be made by techniques well known in the art, such as, for example, the Merrifield solid-phase method described in Science, 232:341–347 (1985). The procedure may use commercially available synthesizers such as a Biosearth 9500 automated peptide machine, with cleavage of the blocked amino acids being achieved with hydrogen fluoride, and the peptides purified by preparative HPLC using a Waters Delta Prep 3000 instrument, on a 15–20 μm Vydac C4 PrepPAK column.

A third approach whereby 26 kd TNF may be obtained is in vitro transcription/translation of the 26 kd molecule. The 26 kd molecule is encoded by a DNA sequence present in the plasmid B11, described in co-pending Cetus patent application, U.S. Ser. No. 670,360, filed Nov. 9, 1984; and U.S. Pat. Nos. 4,677,063 and 4,677,064. The sequence is removed from pB11 by Pst I digestion, cloned into a suitable vector, and translated/transcribed using materials and methods known in the art. See, for example, Transcription and Translation-a Practical Approach (eds. B. D. Hames and S. Higgins) IRL press, 1984; Melton, D. A. et al., (1984) Nucl. Acids Res. 12, 7035; and Pelham and Jackson, Eur. J. Biochem. 67 p. 247. The transcription product, 26 kd TNF may be used as immunogen. However, since in vitro transcription/translation gives a low mount of product, the material so obtained will be used primarily for in vitro immunizations.

Another approach is to transform cells with the DNA sequence that encodes the 26 kd molecule, and to use transformed cells that express the molecule as immunogen, or 26 kd TNF isolated therefrom. This is preferable accomplished by inserting the DNA sequence in pB11 into a suitable vector such as the plasmid pFVXM, which is described in co-pending U.S. patent application, Ser. No. 855,865, titled Infective Drug Delivery System, inventor Kriegler, et al.. pFVXM is on deposit with the American Type Culture Collection and has Accession No. 67,103. pFVXM is a retroviral vector that was derived from the plasmid pEVX described by Kriegler, et al., 1984, in Cell, 38:483. pEVX has a Moloney murine leukemia virus derived splice donor site 3' to the 5'-long terminal repeat. It was previously shown that this splice donor sequence decreases the yield of correctly spliced translational templates of retrovital constructions. Thus, pEVX was engineered to remove the splice donor site, and replaced with an analogous Sma I fragment of the Harvey murine sarcoma virus genome, which lacks the Moloney murine leukemia virus splice donor sequence. The resulting vector, pFVXM, lacks the Moloney murine leukemia virus spliced donor sequence and carries a viral packaging sequence. pFVXM has a convenient Pst I site in which the DNA sequence that encodes the 26 kd TNF species can be inserted.

Thus, pFVXM, or other suitable vectors, is transfected into a appropriate cell type, along with a selectable marker which facilitates selection of transfected cells that express TNF. The marker can be introduced via a second vector, such as for example, pEVX-neo. pEVX-neo is described by Kriegler, et al., 1984, in Cell, 38:483. Transfection may be conducted by methods known in the art, or using a modification of the calcium phosphate method of Wigler, et al., 1978, Cell, 14:725. TNF expressing cells are selected in medium supplemented with an appropriate concentration of G418, obtained from Gibco. An effective way to identify G418-resistant colonies that express TNF activity is to perform a lysis assay with L929 cells. The assay is described in detail in U.S. Pat. No. 4,677,064.

B. Anti-26 kd TNF Antibody

Antibody to 26 kd TNF may be either polyclonal or monoclonal. The antibody is preferably human or humanized, although non-human antibody will perform satisfactorily.

Monoclonal antibody may be produced using TNF peptides/peptide conjugates as described above, or 26 kd TNF, and the procedures described by Kohler, G. and Milstein, C., 1975, Nature, 256:495, or modifications thereof that are known in the art. It is important to note that if 26 kd TNF is used as immunogen, an immune response will be mounted not only to epitopes uniquely associated with 26 kd TNF, but also to the mature, or 17 kd species. Using the screening assays described below, the specificity of antibody produced using 26 kd TNF as immunogen can be discerned. However, because of this inherent limitation using 26 KD TNF, the preferred immunogen is a TNF peptide conjugate.

The initial work of Kohler and Milstein, above, involved fusing murine lymphocytes and drug selectable plasmacytomas to produce hybridomas. Subsequently, the technique has been applied to produce hybrid cell lines that secrete human monoclonal antibodies. The latter procedures are generally described in Abrams, P., 1986, Methods in Enzymology, 121:107, but other modifications are known to those skilled in the art. Regardless of whether murine or human antibody is produced, the antibody secreting cells are combined with the fusion partner and the cells fused with a suitable fusing agent, preferably polyethylene glycol, and more preferably polyethylene glycol 1000. The latter is added to a cell pellet containing the antibody secreting cells and the fusion partner in small amounts over a short period of time accompanied with gentle agitation. After the addition of the fusing agent, the cell mixture is washed to remove the fusing agent and any cellular debris, and the cell mixture consisting of fused and unfused cells seeded into appropriate cell culture chambers containing selective growth media. After a period of several weeks, hybrid cells are apparent, and may be identified as to antibody production and subcloned to ensure the availability of a stable hybrid cell line.

The preferred antibody is human monoclonal antibody which can be prepared from lymphocytes sensitized with 26 kd TNF either in vivo or in vitro by immortalization of antibody-producing hybrid cell lines, thereby making available a permanent source of the desired antibody. In vivo immunization techniques are well known in the art, while in vitro techniques are generally described by Luben, R. and Mohler, M., 1980, *Molecular Immunology*, 17:635, Reading, C. *Methods in Enzymology*, 121 (Part One):18, or Voss, B., 1986, *Methods in Enzymology*, 121:27. A number of in vitro immunization systems have been shown to be effective for sensitizing human B-cells. Reading, C., 1982, *J. of Immun. Methods*, 53:261.

It will be apparent to those skilled in the art that in lieu of immunizing individuals directly with 26 kd TNF, lymphocytes may be isolated from individuals that are experiencing, or have experienced a bacteremic attack. A fraction of these lymphocytes may be sensitized to 26 kd TNF, and can be used to produce permanent antibody secreting hybrid cell lines. For example, immunocompromised human patients are generally susceptible to bacterial infections, particularly those suffering from various malignancies, extensive burns, etc., and lymphocytes isolated therefrom may be a source of antibody secreting cells.

Sensitized lymphocytes can be immortalized by vital transformation. The preferred viral transformation technique for human lymphocytes involves the use of Epstein-barr virus. The virus is capable of transforming human B-cells, and has been used to generate human monoclonal antibodies. Crawford, D. et al., 1983, *J. of General Virology*, 64:697; Kozbor, V. and Roder, J., 1983, *J. Immun. Today*, 4:72.

Another procedure whereby sensitized lymphocytes may be immortalized consist of a combination of the above two techniques, that is viral transformation and cell fusion. The preferred combination consist of transforming antibody secreting cells with Epstein-barr virus, and subsequently fusing the transformed cells to a suitable fusion partner. The fusion partner may be a mouse myeloma cell line, a heteromyeloma line, or a human myeloma line, or other immortalized cell line. PCT Patent Application No. 81/00957; Schlom et al., 1980, *PNAS USA*, 77:6841; Croce et al., 1980, *Nature*, 288:488. The preferred fusion partner is a mouse-human hetero-hybrid, and more preferred is the cell line designated F3B6. This cell line is on deposit with the American Type Culture Collection, Accession No. HB8785. It was deposited Apr. 18, 1985. The procedures for generating F3B6 are described in European Patent Application, Publication No. 174,204.

Techniques applicable to the use of Epstein-Barr virus transformation and the production of immortal antibody secreting cell lines are presented by Roder, J. et al., 1986, *Methods in Enzymology*, 121:140. Basically, the procedure consist of isolating Epstein-Barr virus from a suitable source, generally an infected cell line, and exposing the target antibody secreting cells to supernatants containing the virus. The cells are washed, and cultured in an appropriate cell culture medium. Subsequently, virally transformed cells present in the cell culture can be identified by the presence of the Epstein-Barr vital nuclear antigen, and transformed antibody secreting cells can be identified using standard methods known in the art.

It will be apparent to those skilled in the art that while the preferred embodiment of the instant invention is neutralizing anti-convertase monoclonal antibody, singly or in combination, the antibody (s) may be altered and still maintain biological activity. Thus, encompassed within the scope of the invention is antibody modified by reduction to various size fragments, such as $F(ab')_2$, Fab, Fv, or the like. Also, the hybrid cell lines that produce the antibody may be considered to be a source of the DNA that encodes the desired antibody, which may be isolated and transferred to cells by known genetic techniques to produce genetically engineered antibody. An example of the latter would be the production of single chain antibody having the antibody combining site of the hybridomas described herein. Single chain antibody is described in U.S. Pat. No. 4,704,692. A second example of genetically engineered antibody is recombinant, or chimeric antibody. Methods for producing recombinant antibody are shown in U.S. Pat. No. 4,816,567, inventor Cabilly, et al.; Japanese patent application, Ser. No. 84169370, filed Aug. 15, 1984; U.S. patent application, Ser. No. 644,473, filed Aug. 27, 1984; British patent application 8422238, filed on Sep. 3, 1984; Japanese patent application, No. 85239543, filed Oct. 28, 1985; U.S. patent application, Ser. No. 793,980 on Nov. 1, 1985; U.S. patent application, Ser. No. 77,528, filed Jul. 24, 1987. Also, British patent application, No. 867679, filed Mar. 27, 1986 describes methods for producing an altered antibody in which at least parts of the complementary determining regions (CDRs) in the light or heavy chain variable domains have been replaced by analogous parts of CDRs from an antibody of different specificity. Using the procedures described therein it is feasible to construct recombinant antibody having the CDR region of one species grafted onto antibody from a second species that has its CDR region replaced. A preferred embodiment in this instance is a murine anti-26 kd TNF antibody CDR region that replaces the CDR region of human antibody.

Regardless of the type of antibody, polyclonal or monoclonal etc., it is desirable to purify the antibody by standard techniques as is known in the art, or as described by Springer, 1980, *Monoclonal Antibodies,*: 194, (Eds. Kennett, T. McKearn and K. Bechtol, Plenum Press, New York. Generally this consists of at least one ammonium sulfate precipitation of the antibody using a 50% ammonium sulfate solution. Antibody affinity columns may also be used.

C. Screening of Anti-26 kd TNF Antibody

Cell lines that secrete anti-26 kd TNF antibody that prevents or hinders cleavage of the molecule to lower molecular weight forms of TNF can be identified by assaying culture supernatants, ascites fluid etc., for antibody. The preferred screening procedure consists of two sequential steps. First, hybridomas are identified that are secreting anti-26 kd TNF antibody; and second, the antibody is assayed to determine if it is cleavage site specific. As applied to cell culture supernatants, the initial screening step is preferably done by ELISA assay. The ELISA assay is known in the art, and consists of binding 26 kd TNF to a solid matrix, and detecting the presence of antibody by binding to the 26 kd molecule. Langone, J. and Van Vinakis, H., *Methods of Enzymology*, 92, Part E (1983). However, as this will not distinguish antibody directed solely to 26 kd TNF or the 17 kd species, an alternate first step is to bind TNF peptide conjugates to a solid matrix, and screen against the conjugates, or to follow a positive ELISA result with a immunoprecipitation assay described below.

An additional initial assay for 26 kd TNF antibody is to screen antibodies for their ability to differentially immunoprecipitate 26 kd and 17 kd TNF from a homogeneous phase. For example, supernatant containing the monoclonal antibodies being screened is incubated with labeled 26 kd or 17 kd TNF for an appropriate time to allow antigen/antibody complex to form. After this incubation, the monoclonal antibodies are incubated with anti-xenotypic or anti-isotypic antibodies specific for the monoclonal antibody being screened. These anti-xenotypic or anti-isotypic antibodies are immobilized, for example, on a plastic bead. For example, if the monoclonal antibody being screened is anti-26 kdTNF, then labeled 26 kdTNF will be bound to the bead and thereby immunoprecipitated. The material can be dissociated from the bead using standard techniques and identified as 26 kd TNF by gel electrophoresis, as is known in the art.

To determine if 26 kd TNF antibody is cleavage site specific, the ability of antibody to prevent or retard the conversion of the 26 kd molecule to lower molecular weight forms is monitored. This assay is carried out preferably by incubating 26 kd TNF with a source of convertase activity, and the antibody to be tested. The 26 kd molecule is labelled such that its conversion, or non-conversion as the case may be, can be monitored. It will be understood by those skilled in the art that antibody may be added to the reaction mixture before or after adding the convertase. The order of addition may facilitate identification of the sought after antibody, but it is not determinative. If an antibody has inhibitory activity, and prevents cleavage of the 26 kd molecule, this can be revealed by electrophoretic analysis of the solution which will show little or no conversion of the 26 kd species, and concomitantly little or no lower molecular weight TNF molecules.

To expedite the assay, several culture supernatants may be combined and assayed simultaneously. If the mixture is positive, then media from each well may subsequently be assayed independently to identify those hybridoma(s) that secrete cleavage site specific anti-TNF antibody.

A variety of biological materials are available as sources of convertase activity. These include tissues, cells, or extracts, or fluids associated therewith that are preferably, but not necessarily, of immunologic origin Moreover, established cell lines may also be utilized. Suitable sources would include human peripheral blood mononuclear cells, such as leukocytes or cell lines of leukocyte origin, such as the HL 60 cell line. Thus, the conversion of the 26 kd TNF species to the 17 kd species can be affected by combining the 26 kd species with either intact HL60 cells, or extracts derived therefrom. Further, because the convertase activity is partially membrane associated, it is possible to obtain a membrane fraction that may be utilized.

II. Immunoassay

In another embodiment, the present invention is directed to an immunoassay which can be used to detect 26 kdTNF, which in turn can be used to determine the ratio of 26 kd TNF to 17 kd, or lower molecular weight forms of TNF. The concentrations that are detectable will be in the range of about 1 ng/ml to about 1 µg/ml of either form of TNF. The immunoassay of the present invention is preferably a sandwich assay employing the antibodies disclosed herein, although other assay formats known in the art may also be used.

In practicing the immunoassay method of the present invention, anti-TNF antibody, directed to the 26 kd or 17 kd forms of TNF are immobilized and then incubated with the fluid test sample containing unknown concentrations of these molecules TNF. After allowing for a suitable period of incubation for antigen-antibody complexes to form, the immobilized antibody is incubated with an indicator solution containing a second anti-TNF antibody, either monoclonal or polyclonal, which has been labeled. This second anti-TNF antibody is allowed to incubate with immobilized antibody for a sufficient period of time to allow antigen-antibody complexes to form between the labeled antibody and any TNF bound by the immobilized monoclonal antibody. After this incubation, the immobilized monoclonal antibody is separated from any unbound labeled antibody, and the amount of label remaining bound to the immobilized antibody is measured. This is usually done by measuring a signal related to the amount of label present on the immobilized antibody. The signal, therefore, provides a measure of the amount of TNF in the fluid test sample.

The 26 kd and the 17 kd species may be assayed simultaneously in the same fluid, or separately using different aliquots of the same fluid. If they are measured simultaneously, then the 26 kd and 17 kd antibody must not cross block, and moreover, the 26 kd and 17 kd antibody is preferably of different species origin so that detection can be accomplished with a second anti-TNF antibody that does not cross react. The preferred combination is to measure 26 kd TNF with a mouse monoclonal antibody, and 17 kd TNF with rabbit antibody, and detecting these with differentially labelled mouse and rabbit second antibody, respectively. 17 kd rabbit TNF antibody is known in the art, and readily available.

The antibodies employed in the present invention can be immobilized on any appropriate solid test support by any appropriate technique. The solid test support can be any suitable insoluble carrier material for the binding of antibodies and immunoassays. Many such materials are known in the art, including, but not limited to, nitrocellulose sheets or filters; agarose, resin, plastic (e.g. PVC or polystyrene) latex, or metal beads; plastic vessels; and the like. Many methods of immobilizing antibodies are also known in the art. See, e.g., Silman et al. (1966) Ann. Rev. Biochem. 35: 873; Melrose (1971) Rev. Pure & App. Chem. 21: 83; Cuatrecaas et al. (1971) Meth. Enzym., Vol. 22. Such methods include covalent coupling, direct adsorption, physical entrapment, and attachment to a protein-coated surface. In the latter method, the surface is first coated with a water-insoluble protein such as zein, collagen, fibrinogen, keratin, glutelin, etc. The antibody is attached by simply contacting the protein-coated surface with an aqueous solution of the antibody and allowing it to dry.

Any combination of support and binding technique which leaves the antibody immunoreactive, yet sufficiently immobilizes the antibody so that it can be retained with any bound antigen during a washing, can be employed in the present invention. A preferred solid test support is a plastic bead.

As discussed above, the assay of the present invention employs a labeled anti-TNF antibody to measure the amount of TNF bound by the immobilized monoclonal antibody. The label can be any type that allows for the detection of the antibody when bound to a support. Generally, the label directly or indirectly results in a signal which is measurable and related to the amount of label present in the sample. For example, directly measurable labels can include radio labels (e.g. 125I, 35S, 14C, etc.). A preferred directly measurable label is an enzyme, conjugated to the anti-TNF antibody, which produces a color reaction in the presence of the appropriate substrate. (e.g. horseradish peroxidase/o-phenylenediamine). An example of an indirectly measurable label would be anti-TNF antibody that has been biotinylated. The presence of this label is measured by contacting it with a solution containing a labeled avidin complex, whereby the avidin becomes bound to the biotinylated antibody. The label associated with the avidin is then measured. A preferred example of an indirect label is the avidin/biotin system employing an enzyme conjugated to the avidin, the enzyme producing a color reaction as described above. It is to be understood, however, that the term "label" is used in its broadest sense and can include, for example, employing "labeled" anti-TNF antibodies where the label is a xenotypic or isotypic difference from the mobilized anti-TNF antibody, so that the presence of "labeled" antibodies is detectable by incubation with an anti-xenotypic or anti-isotypic antibody carrying a directly detectable label.

Whatever label is selected, it results in a signal which can be measured and is related to the amount of label in a sample. Common signals are radiation levels (when radioisotopes are used), optical density (e.g. when enzyme color reactions are used) and fluorescence (when fluorescent compounds are used). It is preferred to employ a nonradioactive signal, such as optical density (or color intensity) produced by an enzyme reaction. Numerous enzyme/substrate combinations are known in the immunoassay art which can produce a suitable signal. See, e.g., U.S. Pat. Nos. 4,323,647 & 4,190,496, the disclosures of which are incorporated herein.

Having described what the applicants believe their invention to be, the following examples are presented to illustrate the invention, and are not to be construed as limiting the scope of the invention. For example, variation in the source, type, or method of producing antibodies; different labels and/or signals; test supports of different materials and configurations; different immobilization methods; and different types of TNF may be employed without departing from the scope of the present invention.

EXAMPLE I

Preparation of 26 kd TNF or TNF Peptide Immunogens

A. Membrane Fraction

The vector pFVXM, on deposit with the American Type Culture Collection, Accession No. 67,103, was used to produce a vector pFVXM-TNF6, which contains the DNA sequence that encodes the 26 kd TNF species. The vector, in turn, was used to transfect a cell line from which a membrane fraction can be isolated and used as a source of 26 kd TNF.

To produce the vector, pFVXM-TNF6, the plasmid B11 which contains the cDNA sequence that encodes the 26 kd TNF species was treated with Pst I which excises the coding sequence. The fragment was purified using standard electrophoretic techniques. Next, the vector pFVXM was treated with Pst I, and the Pst I fragment from pB11 containing the 26 kd coding sequence was inserted into the polylinker region of the vector using standard techniques, as described above, to produce pFVX-TNF6.

pFVXM and the plasmid, pB11, were both amplified in *E. coli* strain HB101. Ligation of the fragments was carried out using standard conditions. Plasmid DNA was isolated after the ligation procedure and the correct orientation of the TNF encoding sequences was established by restriction analysis.

Plasmid DNA was prepared according to the procedure of Birnboim and Doly, as described in *Nucleic Acid Research*, 7:1513 (1979). The plasmid DNA was banded twice in cesium chloride, and exhaustively dialyzed against TE buffer consisting of 10 mM Tris, pH 8.0, and 1 mM EDTA.

pFVXM-TNF6 was transfected into psi AM cells to produce a cell line, termed TNF6.8, that expresses the 26 kd TNF species. pFVXM-TNF6 was co-transfected with a second vector, pEVX-neo, which facilitates selection of transfected cells that express TNF. pEVX-neo is described by Kriegler, et al., 1984, *Cell*, 38:483. Transfection was conducted using a modification of the calcium phosphate method of Wigler, et al., 1978, *Cell*, 14:725. Briefly, 10 ug of carrier DNA, diluted with sterile 1 mM Tris, pH 8.1, 0.1 mM EDTA, was added to 100 mm Petri dishes, along with plasmid DNA, 50–1,000 ng per 100 mm Petri dish, followed by the addition of 2.5M $CaCl_2$. This mixture was agitated thoroughly to assure uniform suspension, and an equal volume of 2× HERPES (N-2-hydroxyethyl diperazine N'-2-ethanesulfonic acid) buffered saline, pH 7.1, was added. This mixture was also agitated to assure uniform suspension, after which a precipitate was allowed to form. Thirty minutes later, 1 ml of the suspension was added to psi AM cells in 100 mm Petri dishes containing 10 ml of DMEM supplemented with 10% fetal calf serum. The cultures were incubated at 37° C. for 16 hours and subsequently the medium replaced with fresh growth medium. Next, the growth medium was replaced again with fresh medium, but supplemented with 400 ug/ml of G418, obtained from Gibco.

In order to identify those G418-resistant colonies that express TNF activity, the culture dishes were overlaid with L929 cells at a density of about $7.3 \times 10^4$ cells/$cm^2$. After the cells had attached, the media was aspirated and the cells were overlaid with DMEM supplemented with 10% fetal calf serum and 0.9% Noble agar. After incubation for 18–24 hours, clones surrounded by a lysed zone of L929 cells were isolated using standard cloning cylinders and expanded to a mass culture. The assay for TNF utilizing L929 cells is described in detail in U.S. Pat. No. 4,677,064. One clone, TNF6.8 produced 26 kd TNF. The 26 kd TNF species may be isolated from this cell line in membrane form and used as immunogen.

A membrane fraction is prepared from TNF6.8 cells which consists of harvesting cells from five subconfluent 100 mm dishes. Prior to harvesting the cells, they are rinsed with a buffer containing a protease inhibitor consisting of 10 mM $KPO_4$, pH 7.0, 1 mM phenylmethylsulfonyl fluoride. The solution is removed from the cells, and the cells scraped into a 1.5 ml Eppendorf microfuge tube, and the cells sonicated with a sonifier cell disrupter. This lysate is then spun at 1,000×g for 20 minutes and the supernatant, S-1, saved. The S-1 supernatant is centrifuged at 30,000×g for 10 minutes. The pellet and supernatant, S-3 supernatant, are saved which contained membranous material and the cytosol fraction, respectively. The membrane fraction is used as described below to immunize mice.

B. Peptide Conjugates

Peptides that encompass the cleavage site(s) on 26 kd TNF are synthesized using the solid-phase method, described in more detail in Merrifield R. B., (1985) *Sci.*, 232:341–347, on a Biosearch 9500 automated peptide machine, cleaved with hydrogen fluoride, and purified by preparative HPLC using a Waters Delta Prep 3000 instrument, on a 15–20 µm Vydac C4 PrepPAK column. The following peptides are made:

i) Gln-Ala-Val-Arg-Ser-Ser-Ser,
ii) Gln-Ala-Val-Arg-Ser-Ser-Ser-Arg-Thr-Pro-Ser-Asp-Lys-pro-Val-Ala;
iii) Pro-Leu-Ala-Gln-Ala-Val-Arg-Ser-Ser-Ser-Arg-Thr-Pro-Ser-Asp-Lys-Pro-Val-Ala-His-Val-Val-Ala, Arg-Thr-Pro-Ser-Asp-Lys-Pro-Val-Ala-His-Val-Val-Ala; and
iv) Pro-Leu-Ala-Gln-Ala-Val-Arg-Ser-Ser-Ser-Arg-Thr-Pro.

Before using the peptides to make antibody they are conjugated to a suitable carrier molecule to enhance eliciting an antibody response. These procedures are described in U.S. Pat. No. 4,762,706, inventors McCormick, et al. Suitable carriers are keyhole limpet hemocyanin (KLH) or bovine serum albumin (BSA). The conjugation is achieved via a sulfhydryl group of a cysteine residue that is added to the amino or carboxyl terminal end of the peptides. A heterobifunctional crosslinking reagent, N-maleimido-6-amino caproyl ester of 1-hydroxy-2-nitro-benzene-4-sulfonic acid sodium salt, is prepared by the following procedure.

One molar equivalent (2.24 g) of 4-hydroxy-3-nitro-benzene sulfonic acid sodium salt (HNSA) is mixed together with one molar equivalent (2.06 g) of dicyclohexylcarbodiimide and one molar equivalent (2.10 g) of N-maleimido-6-aminocaproic acid in 25 ml of dimethylformamide (DMF) at room temperature overnight. A white precipitate of dicyclohexyl urea is formed. The precipitate is filtered and 300 ml diethyl ether is added to the mother liquor. After about 10 minutes to 4 hours a gummy solid precipitated from the mother liquor is formed. This solid will contain 58% of active HNSA ester and 42% of free HNSA.

The analysis consists of dissolving a small amount of the precipitate in phosphate buffer at pH 7.0 and measuring the absorbance at 406 nm; this reading provides the mount of unreacted free HNSA which is the contaminating material in the HNSA ester preparation. Addition of very small amounts of concentrated strong base (such as 5N NaOH) instantly hydrolyses the ester formed and a second reading is taken. Subtraction of the first reading from the second yielded the amount of ester in the original material. The solid is then dissolved in DMF and placed on a LH20 Sephadex column and eluted with DMF so that the ester is separated from the contaminating free HNSA. The progress of purification is monitored by thin layer chromatography using during solvents of chloroform, acetone and acetic acid (6:3:1 vol/vol). The product is positively identified as mal-sac HNSA ester by its reactivity with amine. The yield of the pure ester is estimated to be approximately 30% of theoretical; the purified material consist of 99% ester.

The ester thus obtained is found to dissolve fully in water and is stable in water for several hours, provided no nucleophiles are added. When placed in 1N ammonia the ester produces the corresponding amide with a portion hydrolyzed to free acid. The purified ester is found to be stable for extended periods when stored dessicated.

About 0.5 mg of the purified mal-sac HNSA ester is dissolved in 1 ml of distilled water. A 10 µl aliquot of this solution is diluted into 1 ml of 10 mM phosphate buffer at pH 7.0. The absorbance at 406 nm is used to calculate the concentration of free HNSA as described above. When 50 µl of 4.8N sodium hydroxide solution is added to the diluted aliquot of ester and mixed, the absorbance of the solution at 406 nm increases significantly, indicating that the hydroxide nucleophile rapidly hydrolyses the ester to component acid and free HNSA anion.

The difference between the post-base and initial free HNSA concentration represents the concentration of ester. From the actual concentration of ester and protein amino groups the amount of ester to be added to the protein solution to achieve the desired degree of substitution can be calculated.

The purified HNSA ester is then reacted with BSA as follows (the reaction with KLH is similar to this procedure):

A total of 22 mg (20 µmoles) of BSA (of molecular weight 66,296) is dissolved in 2.0 ml of 0.1M phosphate buffer at pH 7.5 to yield a total amine concentration of $1.0 \times 10^{-2}$ moles per liter (assuming 59 lysines/BSA molecule) A calculated amount (11 mg, $2.35 \times 10^{-5}$ moles) of the above-prepared mal-sac HNSA ester (97.7% pure) in powder form is dissolved in 2.0 ml of BSA solution. The reaction is carried out at room temperature. Ten µl aliquots are removed from the solution at timed intervals and are each diluted into 1.0 ml of 0.01M phosphate buffer at pH 7.0. The specutrum of each diluted aliquot is recorded using a Hewlett-Packard spectrophotometer and the absorbance at 406 nm measured. A total of 50 µl of 4.8N NaOH is then added to each aliquot, each aliquot is mixed and its spectrum retaken and the absorbance at 406 nm measured.

From the absorbance at 406 nm before and after addition of base the concentration of ester remaining and the percent ester that reacts are determined for the reaction mixtures. The results show that the reaction rate is essentially linear over a 15 minute period.

At 15 minutes of reaction time, the reaction is stopped by applying the reaction mixture to a PD10 desalting Sephadex G-25 column (Pharmacia, Inc.) equilibrated with 0.1M phosphate buffer at pH 6.0. It is found that $2.6 \times 10^{-3}$ moles/l of the ester reacts and thus 25.9% of the 59 epsilon-amino groups of BSA are presumably substituted. Thus, the product contains 16 mal-sac groups per molecule.

The product of the first reaction, mal-sac-BSA (or mal-sac-KLH), is isolated by applying the reaction mixture to a PD10 desalting Sephadex G-25 column equilibrated with 0.1M phosphate buffer at pH 6.0. The column is eluted with 0.1M phosphate buffer in 1.0 ml fractions. The column elution is followed by monitoring the absorbance spectrum, and peak fractions containing the mal-sac BSA are pooled. The TNF peptides synthesized as described above are added and the pooled mixture is stirred at room temperature overnight. The conjugates are subjected to extensive dialysis against distilled water and lyophilization, and in some cases are analyzed for changes in amino acid composition. These TNF peptide conjugates may be used to immunize animals, or lymphocytes in vitro to produce anti-26 kd TNF antibody.

EXAMPLE II

Immunization With 26 kd TNF or Peptide Immunogens/Production of Hybridomas

A. Murine Monoclonal Antibody

The following describes the immunization of mice with 26 kd TNF or TNF peptide immunogens with the aim of isolating immunized lymphocytes and producing murine hybridomas. Generally, the procedures described in the following references are followed. Shulman et al (1978) Nature 276:269; Oi et al in *Selected Methods in Cellular Immunology*, p 351 (Mischell & Schiigi eds. 1980). Foung et al (1983) Proc. Nat'l Acad. Sci. U.S.A. 79:7484. The general procedures for producing compositions comprising monoclonal antibodies, including the cell lines which produce such compositions, are well known in the art. See, e.g., Gerhard et al. (1978) Proc. Nat'l Acad. Sci. U.S.A. 75: 1510;

*Monoclonal Antibodies* (R. Kennett, T. McKearn, & K. Bechtol eds. 1980); Schreier et al., *Hybridoma Techniques* (1980); *Monoclonal Antibodies and T-Cell Hybridomas* (G. Hammerling, U. Hammerling, & J. Kearney eds. 1981); Kozbor et al. (1982) Proc. Nat'l Acad. Sci. U.S.A. 79: 6651; Jonak et al. (1983) Hybridoma 2: 124; *Monoclonal Antibodies and Functional Cell Lines* (R. Kennett, K. Bechtol, & T. McKearn eds. 1983); Kozbor et al. (1983) Immunology Today 4: 72–79; Shulman et al. (1982) Nature 276: 269–270; Oi et al., in *Selected Methods and Cellular Immunology*, pp. 351–371 (B. Mischell & S. Schiigi eds. 1980); Foung et al. (1983) Proc. Nat'l Acad. Sci. U.S.A. 79: 7484–7488.

Briefly, BALB/c mice are immunized with 5 mg of membranous material, as isolated in Example I, or 0.5 mg of TNF peptides per mouse in phosphate buffered saline (PBS) interperitoneally (I.P.) or intravenously (I.V.), twice at 3 week intervals, and boosted I.V., tail vein, with 0.1 mg in PBS three days prior to fusion. Three days after the I.V. boost, mice are sacrificed, their spleens removed, and the spleenocytes isolated and fused to an immortalized drug selectable myeloma partner cell line. Numerous such myeloma lines are known in the art, most of which are incapable of growth in HAT supplemented cell culture media. A typical myeloma cell line is SP-2/0 Ag 14. Thus, the hybridomas are formed by combining splenocytes and myeloma cells in a 5:1 ratio, which generally consists of $2 \times 10^6$ myeloma cells to $1 \times 10^7$ splenocytes. The cell mixture is pelleted, media removed and fusion affected by the addition of 1.0 ml of 40% (v/v) solution of polyethylene glycol 1500 by dropwise addition over 60 seconds at room temperature, followed by a 60 second incubation at 37° C. To the cell suspension with gentle agitation is added 9 ml of Dulbecco's Modified Eagles medium over 5 minutes. Cell clamps in the mixture are gently resuspended, the cells washed to remove any residual PEG and plated in microtiter plates at about $2 \times 10^5$ cells/well in DMEM supplemented with 20% fetal calf serum. After 24 hours, the cells are fed a 2×solution of hypoxanthine and azaserine selection medium. About two to three weeks later viable hybridoma colonies are apparent, and the media is screened for antibody, as described below. Ascites fluid containing antibody may be produced and purified using Pristane-primed mice as is known in the art.

B. Human Hybridomas/Human Monoclonal Antibody

Peripheral blood lymphocytes are isolated from septic patients, and then infected with Epstein-Barr virus and the infected lymphocytes immortalized by fusion to a selectable myeloma cell line, and the hybrid cell lines so generated isolated and characterized as to antibody production.

More specifically, mononuclear cells are separated on Ficoll-hypaque (Pharmacia), and monocytes depleted from the mixture by adherence to plastic. Standard laboratory techniques were utilized to effect these procedures. Next, nonadherent cells are enriched for antibody producers by antigen-specific panning. Panning is a technique generally known in the art, and involves incubation of a population of antibody secreting cells on a plastic surface coated with the appropriate antigen, in this instance TNF peptides or 26 kd TNF produced as described in Example I by isolating a membranous fraction from 26 kd expressing cells. Those cells that express antibody on their surface bind antigen, and consequently adhere to the plastic surface, whereas cells that do not express cell surface antibody, do not adhere and can be removed by washing. Thus, specific antibody secreting cells are enriched for by this technique.

More specifically, 6-well plates (Costar) are coated with a membrane fraction from the cell line TNF 6.8 that expresses 26 kd TNF. 150 µg of membranous material is coated per well in phosphate buffered saline at 4° C. overnight. The wells are blocked after the overnight incubation period with phosphate buffered saline containing 1% bovine serum albumin for at least 1 hour at 4° C., and subsequently washed with phosphate buffered saline/BSA. Next, $10^7$ lymphocytes in 1 ml of PBS/BSA are added to each well of the six well plates. The lymphocytes are allowed to incubate on the plates for 70 minutes, after which any nonadherent cells are removed by aspiration. The adherent cells are incubated with cell culture medium (IMDM, Sigma Chemical Co., St. Louis, Mo.) containing 10% fetal calf serum.

The adherent cells are subjected to Epstein-Barr virus transformation by adding an equal amount of culture media obtained from growing the Epstein-Barr virus infected marmoset cell line, B95-8, and thus containing the virus, to media bathing the adherent cells. The cells were cultured in this environment at 37° C. for 3 hours, and in this way the lymphocytes in the adherent cell population are subjected to Epstein-Barr infection. Following the infection period, the cells are washed and plated onto 96 well microtiter plates at a density of about $10^4$–$10^5$ cells/well in IMDM medium, plus 10% fetal calf serum, and 30% conditioned medium. The latter is derived from a lymphoblastoid cell fine, preferably JW5. The medium also contains $5 \times 10^{-5}$M 2-mercaptoethanol, 50 µg/ml gentamycin sulfate (Sigma), and 600 ng/ml cyclosporine A (Sandimmune, Sandoz, Basel, Switzerland).

After about 14 to 21 days of incubation, cell culture supernatants are combined and screened for 26 kd TNF binding activity as described below. Positive hybridomas are subcultured at low density, retested for activity, and grown up and fused to the cell line F3B6 using polyethylene glycol and the plate fusion technique known in the art. The latter technique is described by Larrick, J. W., (1985) in *Human Hybridomas and Monoclonal Antibodies*, E. G. Engleman, S. K. H. Foung, J. W., Larrick, and A. A. Raubitschek, Editors, Plenum Press, New York, page 446. F3B6 is a heteromyeloma cell line that is sensitive to growth in media containing 100 µM hypoxanthine, 5 µg/ml azaserine and 5 µM ouabain. Finally, the resulting hybrids are again screened to insure that they produce anti-26 kd TNF antibody.

Media from tissue culture wells containing either murine or human hybridomas, or ascites fluid containing murine antibody is screened for anti-26 kd TNF antibody, and more particularly for antibody that is cleavage site specific, as described in the following example.

EXAMPLE III

Identification of Cleavage Site Blocking Antibody

Media is initially screened for antibody to 26 kd TNF, and antibody that binds to 26 kd TNF is further screened to determine whether it can block proteolytic cleavage of the prohormone.

A membranous fraction containing 26 kd TNF may be isolated using the cell line TNF 6.8, described in Example I, and employed in an ELISA assay to identify 26 kd antibody. The ELSIA assay is shown by Klotz in: Methods in Enzymology, vol. 84, part D, p. 194–201 (1982). Briefly, the assay consists of coating 96-well tissue culture plates (Costar) with a membrane fraction from TNF 6.8. 150 µg of membranous material is coated per well in phosphate buffered saline at 4° C. overnight. The wells are blocked after the overnight incubation period with phosphate buffered saline containing 1% bovine serum albumin for at least 1 hour at 4° C., and subsequently washed with the same solution. 100 ul aliquots of media are added to the tissue culture wells, and the plates incubated at room temperature for 30 minutes, after which the wells are washed 3× with phosphate buffered saline containing 1% bovine serum albumin. Next, goat anti-mouse antisera coupled to alkaline phosphatase is added to the wells and allowed to incubate for an additional 30 minutes at room temperature, followed by washing the wells 3× with phosphate buffered saline containing 1% bovine serum albumin. Finally, to each well is added 150 ul of the alkaline phosphate substrate, p-nitrophenyl phosphate (5 mg/ml) in carbonate buffer, pH 9.8 with 1 mM $MgCl_2$. After 30 minutes the reaction is stopped by the addition of 0.1 ml of 2M NaOH. Hydrolysis of the substrate is indicated by a yellow color that is readily monitored by measuring the absorbance of the solution at 410 nm. Hybridomas from positive tissue culture wells, that is to say, those that are secreting anti-26 kd TNF antibody, are grown up. In order to insure that absorbance at 410 nm is due to the presence of 26 kd TNF antibody, controls are run consisting of omitting 26 kd TNF from the cell culture plates.

An alternate assay for anti-26 kd TNF antibody is to screen cell culture media against TNF peptides using the ELISA described above. In this assay, those antibodies that give a positive signal should be binding to, or very close to the cleavage site(s) on the prohormone. This can be confirmed by as saying for the ability of the antibodies to block proteolysis of the 26 kd molecule.

Antibody that binds to membranous 26 kd or to TNF peptides is assayed for its ability to block cleavage of the 26 kd molecule to lower molecular weight forms. The two most notable lower molecular weight forms have molecular weights of about 17,000 and 15,000. The preferred assay consists of in vitro transcription/translation of the 26 kd molecule, as described above, followed by treatment with convertase in the presence or absence of antibody being tested for cleavage blocking activity. The procedure entails in vitro transcription/translation of the 26 kd molecule encoded by the plasmid B11. Thus, the sequence is removed from pB 11 by Pst I digestion and inserted into the Pst I site of pGEM-3 (obtainable from Promega Biotec). The resulting plasmid, termed pGEM-TNF14, was amplified in *E. coli* using established techniques, and plasmid DNA prepared according to the procedure of Birnboim and Doly, described above. Plasmid DNA was in vitro transcribed by linearizing it with Hind III, and the linearized plasmid templates used to prepare capped transcripts with T7 RNA polymerase and an in vitro transcription kit supplied by Promega Biotec. Transcription was performed using standard techniques as suggested by the manufacturer's instructions.

The mRNA is in vitro translated in the presence of $^{35}$S-cysteine to produce $^{35}$S-cysteine labelled 26 kd TNF. The procedure consists of using a rabbit reticulocyte lysate translation kit, also supplied by Promega Biotec, and following the conditions recommended by the manufacturer.

$^{35}$S-cysteine labelled 26 kd TNF is used to assay for antibody blocking activity as follows. 25 µl of in vitro translated material is combined with 250 µl of uninduced HL60 convertase activity, plus compounds sought to be assayed for inhibitory activity. The convertase is produced by harvesting $2\times10^9$ HL60 cells, and isolating S-1 and P-30 fractions totalling 18 and 6 ml, respectively. 250 uλ of the P-30 fraction is used, although the S-1 fraction may also be used. The assay is carried out at 30° C. for 1 hour, essentially as described above. Next, the reaction mixture is immunoprecipitated with anti-TNF polyclonal antisera and protein A sepharose, pelleted and washed. The bound protein is eluted and electrophoresed. 12% SDS-PAGE gels give good resolution of any 26 kd fragments, and are run according to the procedure of Laemmli (1970) Nature (London) 227:680. The gels are dried and exposed to X-ray film (DuPont, Wilmington, Del.) at −70° C. with intensifying screens, Bonner et al (1974) Eur. J. Biochem. 46:8, and subsequently developed. The gel electrophoretic profiles of 26 kd TNF treated with HL60 convertase and blocking antibody show little or no evidence of lower molecular weight fragments of the prohormone.

EXAMPLE IV

Assay for 26 and 17 kd TNF in Bodily Fluids

The following describes an immunoassay for 26 kd and 17 kd TNF in bodily fluids according to the present invention which, in this embodiment, is a polystyrene bead enzyme immunometric assay (EIMA).

Firstly, it is desirable to identify two antibodies, one that binds to 26 kd TNF and the other that binds to 17 kd TNF. The latter antibody is well known in the art and readily available. Fendly, et al., Hybridoma, vol. 6 no. 4 p. 359 (1987). In essence, the antibodies are non-cross reactive.

Second, a standard curve is developed using known amounts of labelled 26 kd and 17 kd TNF. Such procedures are well known in the art. Briefly, this would consist of titrating both 26 kd and 17 kd TNF in normal human serum. One-half milliliter of each dilution is placed into individual 12×75 mm glass test tubes. Then 6.4 mm polystyrene beads are coated with either anti-26 kd or anti-17 kd antibody using 0.2% glutaraldehyde. Next, the beads are added to each sample and incubated 60 minutes at room temperature, after which the beads are washed three times with 1–2 ml of phosphate buffered saline and counted. The beads may be added to the same separate test tubes. To determine the amount of 26 kd and 17 kd TNF in an unknown sample, the same procedure is repeated, and the results compared to the standard curve.

EXAMPLE V

Clinical Applications of Cleavage Blocking Antibody 26 kd TNF cleavage blocking antibody may be used prophylactically or therapeutically to treat sepsis. Individuals at risk of contracting sepsis, particularly patients undergoing surgery, or those with sepsis may be administered an effective amount of blocking antibody to prevent or reduce the severity of the disease. A typical treatment regime would consist of administering about 5–10 mg of antibody per kilogram of patient body weight. Prophylactically the dose would be given just prior to surgery, and repeated at least once immediately thereafter. Therapeutically the dose would be given every 24–48 hours until remission of the disease is apparent. The initial therapeutic dose would be 25 mg per kilogram of patient body weight, and then reduced to 5–10 mg per kilogram. The antibody may be administered by any number of routes, but the preferred route of administration is i.v.

Variations of the above embodiments will be readily apparent to those of ordinary skill in the art without departing from the scope of the present invention, as described in the following claims.

We claim:

1. A method for prophylactically or therapeutically treating a patient for a disease caused by the presence of a mature hormone in said patient, said mature hormone comprising a 15 kd or a 17 kd TNF and being produced by the protease cleavage of a prohormone form of said mature hormone, said prohormone form comprising a 26 kd TNF, said cleavage being at a prohormone cleavage site, said method comprising administering said patient an effective amount of a monoclonal antibody or an antigen binding fragment thereof that binds to said prohormone TNF at said cleavage site to sterically hinder access of said protease to said cleavage site, thereby preventing or inhibiting formation of said mature hormone TNF.

2. The method of claim 1, wherein said mature TNF has an approximate molecular weight of about 17,000.

3. The method of claim 1, wherein said antibody or said antigen binding fragment thereof has specificity for a sequence of amino acid residues in said 26 kd TNF, said sequence being a member of the group consisting of:

Gln-Ala-Val-Arg-Ser-Ser-Ser,

Gln-Ala-Val-Arg-Ser-Ser-Ser-Arg-Thr-Pro-Ser-Asp-Lys-Pro-Val-Ala,

Pro-Leu-Ala-Gln-Ala-Val-Arg-Ser-Ser-Ser-Arg-Thr-Pro-Asp-Lys-Pro-Val-Ala-His-Val-Val-Ala, and Pro-Leu-Ala-Gln-Ala-Val-Arg-Ser-Ser-Ser-Arg-Thr-Pro.

4. The method of claim 1 or 3, wherein an antigen binding fragment is administered.

5. The method of claim 4, wherein said antigen binding fragment is an F(ab')$_2$, an Fab, or an Fv.

6. The method of claim 5, wherein said antigen binding fragment is humanized.

7. The method of claim 1 or 3, wherein said antibody is humanized.

8. The method of claim 1, wherein said antibody or antigen binding fragment thereof is cleavage site specific.

* * * * *

UNITED STATES PATENT AND TRADEMARK OFFICE
CERTIFICATE OF CORRECTION

PATENT NO. : 5,702,705

DATED : December 30, 1997

INVENTOR(S) : Kriegler et al.

It is certified that error appears in the above-identified patent and that said Letters Patent is hereby corrected as shown below:

On the face of the patent in the section entitled "Related U.S. Application Data," delete the Applicants' claim of priority i.e., "Division of Ser. No. 424,243, Apr. 18, 1995" and substitute therefor --Division of Ser. No. 424,243, Apr. 18, 1995, which is a continuation of Ser. No. 112,600, Aug. 26, 1993, abandoned, which is a continuation of Ser. No. 395,254, Aug. 16, 1989, abandoned.--

Signed and Sealed this

Twentieth Day of April, 1999

*Attest:*

Q. TODD DICKINSON

*Attesting Officer*   Acting Commissioner of Patents and Trademarks